United States Patent [19]
Griesbach et al.

[11] Patent Number: 5,901,706
[45] Date of Patent: May 11, 1999

[54] ABSORBENT SURGICAL DRAPE

[75] Inventors: Henry L. Griesbach, Atlanta; Michael P. Mathis, Marietta; Uyles Woodrow Bowen, Jr., Canton, all of Ga.

[73] Assignee: Kimberly-Clark Worldwide, Inc., Neenah, Wis.

[21] Appl. No.: 08/871,412

[22] Filed: Jun. 9, 1997

[51] Int. Cl.⁶ .................................................. A61B 19/00
[52] U.S. Cl. .......................................... 128/849; 128/852
[58] Field of Search ..................................... 128/849–856

[56] References Cited

U.S. PATENT DOCUMENTS

| | | |
|---|---|---|
| H1340 | 7/1994 | Yetter et al. . |
| 3,276,944 | 10/1966 | Levy . |
| 3,338,992 | 8/1967 | Kinney . |
| 3,341,394 | 9/1967 | Kinney . |
| 3,502,538 | 3/1970 | Petersen . |
| 3,502,763 | 3/1970 | Hartmann . |
| 3,542,615 | 11/1970 | Dobo et al. . |
| 3,550,592 | 12/1970 | Bernardin . |
| 3,554,788 | 1/1971 | Fechillas . |
| 3,636,952 | 1/1972 | George . |
| 3,692,618 | 9/1972 | Dorschner et al. . |
| 3,849,241 | 11/1974 | Butin et al. . |
| 3,881,041 | 4/1975 | Glienke . |
| 4,097,943 | 7/1978 | O'Connell . |
| 4,333,464 | 6/1982 | Nakano . |
| 4,340,563 | 7/1982 | Appel et al. . |
| 4,343,848 | 8/1982 | Leonard, Jr. ............................ 428/156 |
| 4,379,192 | 4/1983 | Wahlquist et al. . |
| 4,588,400 | 5/1986 | Ring et al. . |
| 4,663,220 | 5/1987 | Wisneski et al. . |
| 4,889,136 | 12/1989 | Hanssen . |
| 4,900,554 | 2/1990 | Yanagibashi et al. . |
| 4,902,553 | 2/1990 | Hwang et al. ........................... 428/156 |
| 5,071,648 | 12/1991 | Rosenblatt . |
| 5,284,703 | 2/1994 | Everhart et al. . |
| 5,405,475 | 4/1995 | Kraft et al. . |
| 5,475,903 | 12/1995 | Collins . |
| 5,500,068 | 3/1996 | Srinivasan et al. . |
| 5,500,281 | 3/1996 | Srinivasan et al. . |
| 5,540,979 | 7/1996 | Yahiaoui et al. . |
| 5,546,960 | 8/1996 | Billgren . |
| 5,584,800 | 12/1996 | Scholz et al. . |

FOREIGN PATENT DOCUMENTS

| | | |
|---|---|---|
| 803714 | 1/1969 | Canada . |
| 0006264 | 1/1980 | European Pat. Off. . |
| 0125745 | 11/1984 | European Pat. Off. . |
| 0 532 805 A1 | 3/1993 | European Pat. Off. . |
| 2662603 | 12/1991 | France . |
| 5-200375 | 8/1993 | Japan . |
| 5-228172 | 9/1993 | Japan . |
| 5-293070 | 11/1993 | Japan . |
| 8-80318 | 3/1996 | Japan . |
| 2296216 | 6/1996 | United Kingdom . |
| WO 94/23769 | 10/1994 | WIPO . |
| WO 96/09165 | 3/1996 | WIPO . |

*Primary Examiner*—Michael A. Brown
*Attorney, Agent, or Firm*—Nancy M. Klembus; Jones & Askew, LLP

[57] ABSTRACT

The present invention is directed to novel absorbent surgical drapes containing at least one hydrophilic meltspun fabric layer and a liquid impervious film layer. The meltspun fabric layer may include at least one spunbonded fabric, meltblown fabric or other nonwoven fabric that is made hydrophilic. The filaments or microfibers of the spunbonded or meltblown fabrics may contain a hydrophilic additive in or on the filaments or microfibers. In one embodiment, the film of the surgical drape is breathable. In another embodiment, the film of the surgical drape has anti-slip properties, due to the inherent properties of the film or to a pattern coating of latex or hot melt adhesive on an exposed surface of the film.

24 Claims, 1 Drawing Sheet

ABSORBENT SURGICAL DRAPE

FIELD OF THE INVENTION

The present invention is directed to a single-use, disposable absorbent surgical drape containing one of more layers of hydrophilic fibrous material. The surgical drape of the present invention further comprises a liquid-impervious film bonded to the hydrophilic meltspun fabric.

BACKGROUND OF THE INVENTION

As is generally known, surgical drapes have been designed to greatly reduce, if not prevent, the transmission of liquids through the surgical drape. In surgical procedure environments, such liquid sources include patient liquids such as blood, saliva and perspiration, and life support liquids such as plasma and saline.

Many surgical drapes were originally made of cotton or linen. Such surgical drapes fashioned from these materials, however, permitted transmission or "strike-through" of various liquids encountered in surgical procedures. In these instances, a path was established for transmission of biological contaminates, either present in the liquid or subsequently contacting the liquid, through the surgical drape. Additionally, in many instances, surgical drapes fashioned from cotton or linen provided insufficient barrier protection from the transmission therethrough of airborne contaminates. Furthermore, these articles were costly, and of course laundering and sterilization procedures were required before reuse.

Disposable surgical drapes have largely replaced linen surgical drapes. Advances in such disposable surgical drapes include the formation of such articles from liquid absorbent fabrics and/or liquid impervious films which prevent liquid strike-through. For example, see JP 8080318 assigned to Kyowa Hakko Kogyo K K; U.S. Pat. No. 5,546,960 assigned to Moelnlycke A B; and WO 96/09165 assigned to Exxon. In this way, biological contaminates carried by liquids are prevented from passing through such fabrics. However, in some instances, surgical drapes formed from absorbent fabrics and/or liquid impervious films, while being liquid and airborne contaminate impervious, sacrifice other drape properties, such as meeting Class 1 flammability requirements per NFPA 702-1980, tear strength, being relatively "lint free" (not containing loose fibrous elements), and drape slippage. Class 1 flammability requirements are met when a material takes 20 seconds or greater for a flame from a standardized ignition source to spread 5 inches according to NFPA 702-1980 test conditions.

In some instances, surgical drapes fashioned from liquid absorbent fabrics alone, such as fabrics formed from hydrophilic fibers, sufficiently absorb liquids and are more breathable and thus more comfortable to the wearer than nonporous materials. However, these improvements in comfort and breathability provided by such nonwoven fabrics have generally occurred at the expense of barrier properties of the drape.

The need for improved liquid absorptivity and fluid impervious barrier properties has resulted in the introduction of hydrophilic fibers into various layers of surgical drapes. One commercially available drape, assigned to Moelnlycke AB, and sold under the tradename Klinidrape®, comprises a liquid absorbent nonwoven top sheet containing inherently hydrophilic rayon staple (discontinuous) fibers, a fluid-impermeable intermediate sheet of polyethylene, and a bottom sheet of cellulose wadding. Although the Klinidrape® has liquid absorptivity and fluid impermeability, the drape produces relatively numerous lint particles and does not pass the Class 1 flammability requirements of NFPA 702-1980.

In order to improve drape strength without drastically increasing the drape density, spunbonded fabrics containing continuous synthetic filaments have been laminated with films and incorporated into surgical drapes. Such laminate fabrics are relatively low in cost. One such laminated fabric is a non-absorbing surgical drape, disclosed in GB 2296216, which is assigned to Kimberly-Clark Worldwide, and comprises a multilayer film bonded to a support layer, such as a hydrophobic spunbonded fabric layer. A similar laminate, disclosed in WO 96/09165 and assigned to Exxon, comprises a microporous film adhesively bonded between an outer nonwoven layer containing hydrophobic spunbonded filaments and a hydrophilic nonwoven inner layer. With respect to applications as surgical drapes, the film component provides a barrier to fluid, while the spunbonded component provides strength to the drape. However, since the spunbonded fabric component of the above laminates fail to exhibit hydrophilic properties, the drapes lack fluid absorbency.

One composite fabric, a spunlaced fabric/"dimpled" film laminate, disclosed in U.S. Pat. No. 5,546,960 to Billgren and assigned to Moelnlycke A B, consists of an absorbent fabric bonded to a film with applications targeted for use in surgical garments, such as gowns and drapes. The above laminate is described as possessing absorptivity and barrier properties with respect to fluids. The absorbent fabric is specified as a spunlaced nonwoven, which is different from the hydrophilic meltspun fabric of the present invention.

Another composite fabric, disclosed in U.S. Pat. No. 4,379,192 to Wahlquist et al., comprises an absorbent fabric bonded to an impervious film with applications targeted for use in surgical garments, such as gowns and drapes. The above laminate is described as possessing absorptivity and barrier properties with respect to liquids. The absorbent fabric is specified as a meltblown nonwoven, which may also contain a surface layer in the form of a continuous and randomly dispersed fiber layer.

None of the laminates disclosed above address the need to reduce the slippage that is prone to occur between the exposed surfaces of a drape or adjacent drapes.

Consequently, there exists a need in the art for surgical drapes and methods for making the same, which provide liquid absorptivity, liquid strike-through protection, drape strength and reduced drape slippage at a relatively low cost. Such improved materials and methods are provided by the present invention and will become more apparent upon further review of the following specification and claims.

SUMMARY OF THE INVENTION

The absorbent surgical drapes of the present invention include at least one layer of hydrophilic meltspun fabric bonded to a film. Desirably, the hydrophilic meltspun fabric is provided as an outermost layer of the surgical drape and the inner film layer contacts a patient. In a preferred embodiment, the hydrophilic meltspun fabric comprises a "hydrophilic" spunbonded fabric. Although the filaments of spunbonded fabrics are typically made from hydrophobic polymeric material, the spunbonded fabrics of the present invention are made hydrophilic by incorporating a hydrophilic chemical additive in or on the spunbonded filaments. Other preferred embodiments include meltspun fabrics comprising at least one spunbonded fabric layer in combination with one or more meltblown fabric layers, wherein one or more of the fabric layers are made hydrophilic by incorporating a hydrophilic chemical additive in or on the respective fabrics. Desirably, the film is a breathable film, allowing the passage of vapor and gas therethrough, but providing a barrier against liquid. In a further preferred embodiment, the exposed film surface exhibits anti-slip attributes; such attributes can be obtained by proper selection of the film and/or by at least partially coating the film with a latex or pressure sensitive or hot melt adhesive that increases the coefficient of friction of the film's surface.

Desirably, the surgical drapes of the present invention are formed from one or more nonwoven fabric layers. In the case where the absorbent drape comprises multiple fabric layers, the layers are generally positioned in a juxtaposed or surface-to-surface relationship and all or a portion of the layers may be bound to adjacent layers. Each type of nonwoven fabric may also be formed from a plurality of separate nonwoven webs wherein the separate nonwoven webs are similar or different from one another. One or more of these inherently hydrophobic fabrics are made hydrophilic by incorporating hydrophilic chemical additives in or on the filaments or both.

The polymeric materials used to form the absorbent fabrics described above include inherently hydrophobic polyolefins. For example, suitable polyolefins include, but are not limited to, polypropylene, polyethylene, or co-polymers thereof. Such polymeric materials may be formed into monocomponent and multicomponent, or conjugate, filaments and used alone or in combination with other synthetic fibers to render nonwoven fabrics.

The hydrophilic chemical additives incorporated into the filaments used to form the hydrophilic spunbonded fabric and the other, optional, nonwoven fabrics described above, may include any additive which is thermally stable at temperatures up to 300° C. and sufficiently phase separates such that the additive migrates from the bulk of the polymer fiber towards the surface of the polymer fiber as the fiber cools without requiring the addition of heat. Once at the polymer surface, the chemical additive changes the hydrophobicity of the polymer surface such that the surface of polymer rapidly wets upon contact with an aqueous fluid. Such chemical additives include, but are not limited to, one or a combination of additives selected from the following classes of additives: (i) polyoxyalkylene modified fluorinated alkyls, (ii) polyoxyalkylene fatty acid esters, (iii) polyoxyalkylene modified polydimethyl siloxanes and PEG-terephthalate (polyethylene glycol modified terephthalate) and (iv) ethoxylated alkyl phenols. The choice of one or more chemical additives depends upon, for example, cost, compatibility with the polymeric material, and the overall contribution to the properties of the finished drape.

For the embodiments where the hydrophilic properties of the absorbent fabric are due to hydrophilic chemical additives added on the surfaces of the fabric filaments, the hydrophilic additives may include any additive which is thermally stable at temperatures up to 100° C. Once on the filament surface, the chemical additive changes the inherent hydrophobicity of the filament surface such that the filament surface wets upon contact with an aqueous fluid. Such chemical additives include, but are not limited to, those identified above and having thermal stabilities up to 100° C. Any such chemical is suitable for the present invention as long as the chemical does not negatively impact desired properties of the surgical drape. Further, the hydrophilic spunbonded fabrics and other nonwoven fabrics comprising the absorbent fabric of the invention may also be treated with any known antistatic agent.

In a further embodiment, the surgical drape of the present invention includes a hydrophilic meltspun fabric and a film laminated thereto. The drape may further include a coating of anti-slip material on the exposed surface of the film to increase the dynamic coefficient of friction of the film surface. The coating material may be present on a portion of the film surface or may completely coat the film surface. Desirably, the coating material is applied to the film surface in a dot, grid or similarly designed pattern, to coat a portion of the film surface area. Suitable coating materials include, but are not limited to, latex, pressure sensitive, or hot melt adhesives. Desirably, the dynamic coefficient of friction value of the exposed surface of the film with respect to the absorbent fabric of the surgical drape is greater than about 0.4 as a result of the film material, the coating material, or both.

The surgical drapes of the present invention may also be provided with one or more fenestrations within the surgical drape. Each fenestration is generally sized for overlying the operating site of the patient and for providing a health care provider a means of accessing the site. The fenestration extends through one or more or the surgical drape layers and may vary in size depending upon the intended use of the surgical drape. Additionally, the surgical drape may contain other components such as an incise material, a release layer over an incise material, a pouch for storing surgical equipment, and any other surgical drape component known to those of ordinary skill in the art.

The surgical drapes of the present invention may be manufactured by any method of making surgical drapes known to those of ordinary skill in the art. The hydrophilic meltspun fabric may be prepared by adding a hydrophilic chemical additive to the polymer melt and subsequently forming meltspun filaments or fibers. Alternatively, the hydrophilic chemical additive may be coated onto the meltspun fabric. These methods may also be used to render hydrophilic other nonwoven fabrics made from inherently hydrophobic polyolefins that are used in conjunction with the meltspun fabric in the absorbent drape. The hydrophilic meltspun fabric, and other optional nonwoven fabrics, that comprise the absorbent drape may be further processed by bonding a film on an outer surface of the fabric thermally, adhesively or by extrusion coating. Additionally, an exposed surface of the film of the meltspun fabric/film laminate may be coated with an anti-slip material to reduce drape slippage. Suitable coating methods include, but are not limited to, solution coating, gravure coating, print coating, etc.

The surgical drapes of the present invention satisfy the need in the art for hydrophilic surgical drapes, which provide improved liquid absorptivity, breathability and comfort, as well as, improved drape strength and reduced drape slippage while meeting the Class 1 flammability requirements of NFPA 702-1980 (flame propagation of 20 seconds or greater) and having relative low levels of lint particles.

These and other objects, features and advantages of the present invention will become apparent after a review of the following drawings and detailed description of the disclosed embodiments and the appended claims.

DETAILED DESCRIPTION OF THE INVENTION

Figure 1:
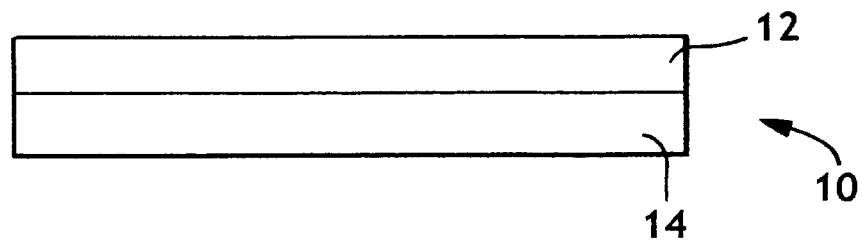
FIG. 1 depicts a portion of a cross-section of an embodiment of the surgical drape of the present invention.
Figure 2:
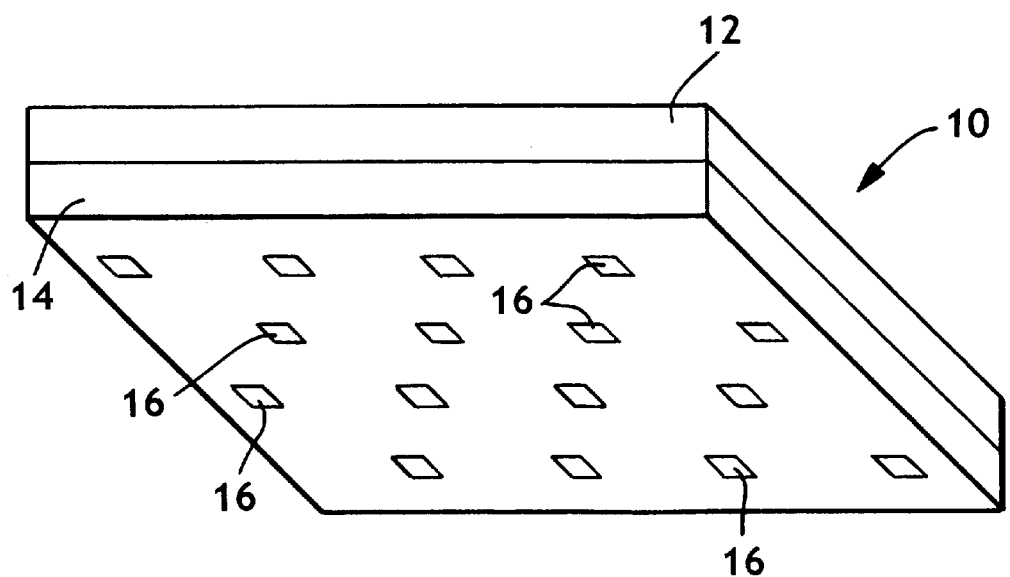
FIG. 2 depicts a perspective view of the bottom surface of an alternate embodiment of the surgical drape of the present invention.

The surgical drapes of the present invention comprise one or more distinct absorbent hydrophilic layers. The surgical drape, as shown in FIG. 1 at 10, may contain at least one absorbent layer comprising a "hydrophilic" meltspun fabric 12. Although the fibrous components of the meltspun fabric are made from hydrophobic polymeric materials, the meltspun fabric is made hydrophilic by incorporating a hydrophilic chemical additive in or on the meltspun fibrous components of the fabric. Desirably, the hydrophilic meltspun fabric is provided as an outermost layer of the surgical drape. In further embodiments, the hydrophilic meltspun fabric is combined with at least one other layer, which provides additional properties to the surgical drape. In a preferred embodiment, the surgical drape includes an outermost layer of a hydrophilic meltspun fabric, in the form of a spunbonded fabric, and an inner film layer 14, which, when in use, contacts a surgery patient. Desirably, the film is a breathable film, allowing the passage of vapor and gas therethrough, but providing a barrier against liquid. Each of the layers of the surgical drape may have a shape and size independent from one another; however, each layer is generally similar in shape and desirably coextensive with the other layers.

Desirably, the surgical drapes of the present invention are formed from one or more nonwoven fabric layers. In the case of multiple layers, the layers are generally positioned in a juxtaposed or surface-to-surface relationship and all or a portion of the layers may be bound to adjacent layers. The nonwoven fabric may also be formed from a plurality of separate nonwoven webs wherein the separate nonwoven webs are similar or different from one another.

As used herein, the term "nonwoven fabric" refers to a fabric that has a structure of individual fibers or filaments which are randomly and/or unidirectionally interlaid in a mat-like fashion. Nonwoven fabrics can be made from a variety of processes including, but not limited to, air-laid processes, wet-laid processes, hydroentangling processes, staple fiber carding and bonding, and solution spinning. Suitable nonwoven fabrics include, but are not limited to, spunbonded fabrics, meltblown fabrics, wet-laid fabrics, hydroentangled fabrics, spunlaced fabrics and combinations thereof.

As used herein, the term "meltspun fabric" refers to a nonwoven web of filaments or fibers, which are formed by extruding a molten thermoplastic material, or coextruding more than one molten thermoplastic material, as filaments or fibers from a plurality of fine, usually circular, capillaries in a spinnerette with the diameter of the extruded filaments or fibers. Meltspun fabrics include, but are not limited to, spunbonded fabrics and meltblown fabrics and are characterized as having thermal bonding junctions throughout the fabric.

As used herein, the term "spunbonded fabric" refers to a web of small diameter continuous filaments which are formed by extruding a molten thermoplastic material, or coextruding more than one molten thermoplastic material, as filaments from a plurality of fine, usually circular, capillaries in a spinnerette with the diameter of the extruded filaments then being rapidly reduced, for example, by non-eductive or eductive fluid-drawing or other well known spunbonding mechanisms. These small diameter filaments are substantially uniform with respect to each other. The diameters that characterize these filaments range from about 7 to 45 microns, preferably from about 12 to 25 microns. The production of spunbonded nonwoven webs is illustrated in patents such as Appel et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, the term "meltblown fabrics" refers to a fabric comprising fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameters, which may be to "microfiber" diameter. Thereafter, the meltblown fibers are carried by the high-velocity gas stream and are deposited on a collecting surface to form a web of randomly disbursed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved Device for the Formation of Super-Fine Thermoplastic Fibers" by K. D. Lawrence, R. T. Lukas, and J. A. Young; and U.S. Pat. No. 3,849,241 issued Nov. 19, 1974 to Buntin et al.

As used herein, the term "microfibers" means small diameter fibers having an average diameter not greater than about 100 microns, for example, having a diameter of from about 0.5 microns to about 50 microns. More specifically microfibers may also have an average diameter of from about 1 micron to about 20 microns. Microfibers having an average diameter of about 3 microns or less are commonly referred to as ultra-fine microfibers.

As used herein, the term "wet-laid fabrics" refers to fabrics formed by a process, such as a paper-making process, wherein fibers dispersed in a liquid medium are deposited onto a screen such that the liquid medium flows through the screen, leaving a fabric on the surface of the screen. Fiber bonding agents may be applied to the fibers in the liquid medium or after being deposited onto the screen. Wet-laid fabrics may contain natural and/or synthetic fibers.

As used herein, the term "hydroentangle" or "hydroentangling" refers to a process wherein a web of material consisting of one or more types of fibers are subjected to high-velocity water jets, which entangle the fibers to achieve mechanical bonding.

As used herein, the term "spunlaced fabrics" refers to a web of material consisting of one or more types of non-continuous fibers, where the fibers are hydroentangled to achieve mechanical bonding without binder materials or thermal bonding.

The surgical drapes of the present invention comprise at least one hydrophilic meltspun fabric and a film attached to the meltspun fabric. Desirably, the surgical drapes comprise a hydrophilic spunbonded fabric. More desirably, the surgical drapes comprise a hydrophilic spunbonded fabric and a breathable film attached to the spunbonded fabric.

As used herein, the term "breathable" refers to a material which allows the passage of vapor and/or gas therethrough, but forms a barrier against the passage therethrough of liquids. Breathable films are well known in the art and may be produced by any known method.

The absorbent drape of the present invention may comprise monocomponent and/or multicomponent, or conjugate, synthetic filaments and/or fibers that may be produced from a wide variety of thermoplastic polymers that are known to form fibers. Suitable polymers for forming the drapes of the present invention include, but are not limited to, polyolefins, e.g., polyethylene, polypropylene, polybutylene, and the like. Of the suitable polymers for forming conjugate fibers, particularly suitable polymers for the high melting component of the conjugate fibers include polypropylene, copolymers of propylene and ethylene and blends thereof, polyesters, and polyamides, more particularly polypropylene. Particularly suitable polymers for the low melting component include polyethylenes, more particularly linear low density polyethylene, high density polyethylene and blends thereof. Most suitable component polymers for conjugate fibers are polyethylene and polypropylene.

In addition, the polymer components may contain thermoplastic elastomers blended therein or additives for enhancing the crimpability and/or lowering the bonding temperature of the fibers, and enhancing the abrasion resistance, strength and softness of the resulting webs. For example, the low melting polymer component may contain about 5 to about 20% by weight of a thermoplastic elastomer such as an ABA' block copolymer of styrene, ethylenebutylene and styrene. Such copolymers are commercially available and some of which are identified in U.S. Pat. No. 4,663,220 to Wisneski et al. An example of a highly suitable elastomeric block copolymer is KRATON G-2740. Another group of suitable polymer additives is ethylene alkyl acrylate copolymers, such as ethylene butyl acetate, ethylene methyl acrylate and ethylene ethyl acrylate. The suitable amount to produce desired properties is from about 2 wt. % to about 50 wt. %, based on the total weight of the low melting polymer component. Yet other suitable polymer additives include polybutylene copolymers and ethylene-propylene copolymers.

In a preferred embodiment of the present invention, one or more hydrophilic chemical additives are added to the polymer melt to form hydrophilic fibrous material for hydrophilic meltspun fabrics. Particularly useful hydrophilic chemical additives include hydrophilic additives, which are generally nontoxic, have a low volatility and are sufficiently soluble in the molten or semi-molten polymer. Additionally, the hydrophilic chemical additive is desirably thermally stable at temperatures up to 300° C. and sufficiently phase separates such that the additive migrates from the bulk of the polymer fiber towards the surface of the polymer fiber as the fiber cools without requiring the addition of heat. Once at the polymer surface, the chemical additive changes the hydrophobicity of the polymer surface such that the surface of polymer rapidly wets upon contact with an aqueous fluid. Such chemical additives include, but are not limited to, one or a combination of additives selected from the following classes of additives: (i) polyoxyalkylene modified fluorinated alkyls, (ii) polyoxyalkylene fatty acid esters, (iii) polyoxyalkylene modified polydimethyl siloxanes and PEG-terephthalate (polyethylene glycol modified terephthalate) and (iv) ethoxylated alkyl phenols. An example of a suitable polyoxyalkylene modified fluorinated alkyl is FC-1802, a product of the Minnesota Mining and Manufacturing Company. An example of a suitable polyoxyalkylene fatty acid ester is PEG-400 ML, a product of Henkel Corporation/Energy Group. An example of a suitable polyoxyalkylene modified polydimethyl siloxane is MASIL® SF-19, a product of PPG Industries. An example of suitable ethoxylated alkyl phenol is Triton®* 102, a product of Union Carbide.

The hydrophilic chemical additives may be added to the meltspun fabric following fabric formation. Suitable methods of applying the hydrophilic chemical additives to a meltspun fabric include, but are not limited to, particle coating, spray coating, or solution coating.

Generally, the concentration of the chemical additive in or on the filaments or fibers that comprise the meltspun fabric (e.g., spunbonded filaments or meltblown microfibers) is desirably about 0.1 wt % to about 5.0 wt %, more desirably about 0.25 wt % to about 5.0 wt %, and most desirably about 1.0 wt % to about 1.5 wt %. The choice of one or more chemical additives depends upon, for example, cost, compatibility with the polymeric material, and the overall contribution to the properties of the finished drape.

The hydrophilic meltspun fabrics provide superior liquid absorptivity to the surgical drapes of the present invention compared to conventional, namely hydrophobic, spun-bonded fabric-containing surgical drapes or provide equivalent liquid absorptivity without being flammable compared to commercially available absorbent drapes. Desirably, the hydrophilic meltspun fabrics have a basis weight of from about 15 to about 140 grams per square meter (gsm). More desirably, the hydrophilic meltspun fabrics have a basis weight of from about 20 to about 60 grams per square meter (gsm).

The hydrophilic meltspun fabrics of the surgical drapes of the present invention may also be treated with or contain various chemicals in order to impart desirable characteristics. Any such chemical is suitable for the present invention as long as the chemical does not negatively impact desired properties of the surgical drape. For example, the hydrophilic meltspun fabrics may be treated with any known antistatic agent, fire retardant, or other desirable chemical finish.

In a further embodiment, the surgical drape of the present invention includes a hydrophilic meltspun fabric, as described above, and one or more additional fabric layers bonded thereto. In a preferred embodiment, a meltblown fabric is attached to a hydrophilic meltspun fabric in the form of a spunbonded fabric. The microfibers of the meltblown fabric may contain a hydrophilic chemical additive therein or may be subsequently coated with a hydrophilic chemical additive, prior to or after lamination with the spunbonded fabric.

In a further embodiment, the surgical drape of the present invention includes a hydrophilic meltspun fabric or laminate, as described above, and a layer in the form of a liquid-impervious film. The film layer provides liquid strike-through protection to the surgical drape and may also provide properties such as breathability and particulate filtration. Suitable materials for forming the film layer include, but are not limited to, polypropylenes, polyethylenes, copolymers, as well as blends thereof. The film is desirably formed from a material which is liquid impermeable and vapor permeable. Further, the film tested against the top side of the absorbent fabric of the surgical drape desirably has a dynamic coefficient of friction greater than about 0.4 as measured by ASTM D1894. This value is a measure of the propensity of slippage between stacked drapes. More desirably, the film has a dynamic coefficient of friction greater than about 0.7. Even more desirably, the film has a dynamic coefficient of friction greater than about 0.85. For example, one film comprises a low density polyethylene, Dow Chemical's Engage® 8002, which has a dynamic coefficient of friction of about 1.68 when measured against a polypropylene spunbonded fabric which has been topically treated to be made hydrophilic.

The film may also contain filler material in order to impart desirable properties to the film such as increased coefficient of friction and/or air permeability. The amount of filler material may vary widely as long as the liquid impermeability of the film is maintained. One preferred breathable film comprises a polymeric blend of polypropylene and Catalloy® polymer filled with about 60 wt % calcium carbonate. Desirably, the film has a film thickness of from about 0.3 to about 1 mil. More desirably, the film has a film thickness of from about 0.5 to about 0.8 mil. Desirably, the film has a film basis weight of less than about 25 grams per square meter (gsm). More desirably, the film has a film basis weight of less than about 20 gsm.

The film may be adhesively attached to the hydrophilic meltspun fabric using any known adhesive that ensures that the layers remain attached during use. Alternatively, when the film and meltspun fabric contain components that are thermally miscible with and adherent upon thermal activation, the film may be thermally bonded to the hydrophilic meltspun fabric by heating the film, fabric, or film and fabric to a sufficient temperature and applying sufficient pressure to form unitary, cohesive bonds among the components of the film, fabric or film and fabric. Moreover, the film may be extrusion coated onto the hydrophilic meltspun fabric.

In a further embodiment, the surgical drape of the present invention includes a hydrophilic meltspun fabric and a film layer as described above, and further includes a coating of anti-slip material on the exposed surface of the film to increase the dynamic coefficient of friction of the film surface with respect to the top surface of the fabric. The coating material may be present on a portion of the film surface or may completely coat the film surface. Desirably, the coating material 16 is applied to the film surface in a dot, grid or similarly designed pattern, to coat a portion of the film surface area. Suitable coating materials include, but are not limited to, latex, pressure sensitive or hot melt adhesives. Desirably, the dynamic coefficient of friction value of the exposed surface of the film with respect to the top side of the absorbent fabric of the surgical drape is greater than about 0.7 due to the film material, the coating material, or the combination thereof. More desirably, the dynamic coefficient of friction value of the exposed surface of the coated film is greater than about 0.85. Even more desirably, the dynamic coefficient of friction value of the exposed surface of the coated film is greater than about 1.0. Most desirably, the dynamic coefficient of friction value of the exposed surface of the coated film is greater than about 1.2.

The surgical drapes of the present invention, formed from at least one layer of hydrophilic meltspun fabric, may also be provided with one or more fenestrations within the surgical drape. The fenestration is generally sized for overlying the operating site of the patient and for providing a health care provider a means of accessing the site. The fenestration may extend through one or more of the surgical drape layers and may vary in size depending upon the intended use of the surgical drape. Additionally, the surgical drape may contain other components such as an incise material, a release layer over an incise material, a pouch for storing surgical equipment, etc.

While the focus has been directed to surgical drapes, there are many other applications for the drapes of the present invention. Other applications include, but are not limited to, patient prep pads, examination table covers, patient mattress bed covers or liners, and the like.

The present invention is described above and below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

The following tests were used to compare the absorbent surgical drapes of the present invention to other absorbent fabrics:

Water Capacity: This test measures the amount of water absorbed by an unconstrained sample in 3 minutes and retained by the sample after being vertically suspended for 1 minute. The result is expressed as weight % retained with respect to the sample's dry weight.

Water Rate: This test measures the time in seconds needed for 10 ml of water to be visually absorbed into the surface of a sample.

Dynamic Coefficient of Friction (ASTM D1894): ASTM D1894 tests the dynamic coefficient of friction of a sample drape's top side against the drape's bottom side to obtain a measure of the propensity of slippage between stacked drapes.

Grab Tensile (ASTM D5034-90 and ASTM D5035-90): This test measures the peak load and elongation of a sample. A one inch square of specimen area is clamped at both ends of a 4"×6" specimen, with the specimen typically oriented in a machine direction (MD) or a cross machine direction (CD). The specimen is pulled at a constant rate of extension and the load and extension just before the point of rupture is recorded.

Flammability (NFPA-702-1980): This test measures the flame resistance of materials when they are in prolonged contact (30 seconds) with the source of ignition. The test measures the rate of burning. A standardized flame is impinged for 30 seconds on the lower edge of a 2½"×6" specimen mounted at a 45 degree angle. The time for the flame to spread 5 inches is recorded in seconds.

EXAMPLE 1

Three absorbent laminates, Samples 1A, 1B and 1C, were produced, each comprising a top ply of hydrophobic polypropylene spunbonded filaments and a fluid impervious film. The basis weight of each top ply for Samples 1A, 1B and 1C was 0.7 ounces per square yard (osy), 0.85 osy and 1.0 osy, respectively. The film was made from a blend of polypropylene and Catalloy® polymer.

In each of the laminates, the polypropylene spunbonded fabric was thermally bonded first via a calendering system consisting of a steel pattern roll against a steel anvil roll. The pattern roll had a repeating arrangement of pin elements, with each pin element having a surface area of about 0.0005 to 0.00075 in$^2$, to produce a total bond area of about 14.5 to 20% of the fabric surface area. The polypropylene spunbonded fabric was subsequently thermally bonded (using another bond pattern) to the film immediately after the film had been stretched to a final basis weight of 0.31 osy (10.5 gsm); the laminating bond pattern imparted about 15% bonded area of the spunbonded fabric to the film. After the polypropylene spunbonded fabric was laminated to the film, the laminate was allowed to retract slightly, about 10%, which formed void space between the fabric and film. After the laminate had retracted, the polypropylene spunbonded side of the laminate was topically treated with a combination of a surfactant and an antistat. The surfactant was Glucopon 220 UP (Henkel Corporation) delivered to give about 0.45 wt % solids add-on, and the antistat was DuPont's Zelec KC, delivered to give about 0.09 wt % solids add-on.

The above laminates were compared to Moelnlycke's Klinidrape® Universal Set Drape (Com.1). This commercially available absorbent drape is made of an absorbent top ply, a fluid impervious film center ply, and a cellulose wadding bottom ply. The top ply, a nonwoven consisting of carded rayon staple fibers bonded into a fabric with a chemical binder system (i.e. latex), and the bottom ply, a cellulose wadding tissue ply, are made from inherently wettable fibers. The results of the comparison are given below.

| Sample | Com. 1 | Ex. 1A | Ex. 1B | Ex. 1C |
|---|---|---|---|---|
| Laminate Basis Wgt, GSM | 75 | 33 | 38 | 46 |
| Spunbond Basis wgt, GSM | 0 | 24 | 28 | 35 |
| Water Capacity, % | 554 | 671 | 583 | 500 |
| Water Rate, seconds | 0.8 | 40.7 | 9.6 | 24.5 |
| Dynamic Coefficient of Friction | 0.64 | 0.49 | 0.50 | 0.44 |
| CD Grab Tensile | | | | |
| Peak Load, gm | 3668 | 5221 | 6311 | 8853 |
| Peak Elongation, % | 36 | 66 | 67 | 66 |
| Flammability, seconds | | | | |
| MD | 5.7 | 30 | 27.9 | 28 |
| CD | — | 30 | 30 | 30 |

Flammability testing for Moenlycke's Klinidrape® Universal Set Drape was tested with and without the cellulose wadding bottom ply. The measured values with and without cellulose wadding differed by only 0.2 seconds. Hence, the absorbent fabric, consisting of rayon staple fibers, is as flammable as the cellulose wadding.

As can be seen from the above data, the polypropylene spunbonded/film laminates of the present invention have greater hydrophobic tendency (water rate), greater strength (grab tensile), and an increased propensity to slip (dynamic coefficient of friction) versus Moelnlycke's Klinidrape® Universal Set Drape. However, the laminates of the invention are absorbent, similar to the Klinidrape® drape, as determined by water capacity values, and they have more desirable values with respect to flammability (the drapes of the present invention meet the 20 second or greater flame propagation criteria for a Class 1 material according to NFPA 702-1980 test conditions).

EXAMPLE 2

A laminate was made as in Example 1 with the following distinctions. The film was made from a blend of Rexene W107 polypropylene and a Union Carbide 6D82 copolymer (3% ethylene, 97% propylene), and contained about 65 wt % calcium carbonate filler. The film was air permeable and fluid impervious after it was stretched to a 0.61 osy final basis weight. The film was thermally bonded to a polypropylene spunbonded fabric using the same bond pattern used to bond the polypropylene spunbonded fabric as described in Examples 1; however, there was minimal retraction allowed after lamination. The result of these two processing factors was a laminate wherein the polypropylene spunbonded ply remained in close contact to the film at all locations (rather than only at bond points as occurred in Example 1). The polypropylene spunbonded was then topically treated with the Zelec KC antistat (0.9 wt % add-on) and with a surfactant mixture of Alchovel Base N-62 (ICI Americas, Inc.) and Glucopon 220 UP (Henkel Corporation), in a 3:1 ratio respectively, at about 0.5 wt % add-on.

The laminate of Example 2 was compared to Kimberly-Clark's SMS Thermal Laminate (Com.2) and Sample C of Example 1. Kimberly-Clark's SMS Thermal Laminate is a commercially available non-absorbent medical fabric comprising polypropylene spunbonded exterior plies and a center ply of polypropylene meltblown. The plies are thermally laminated together. One side of the polypropylene spunbonded is topically treated with DuPont's Zelec KC antistat. Results of the tests are given below.

| Sample | Com. 2 | Ex. 1C | Ex. 2 |
|---|---|---|---|
| Laminate Basis Wgt, GSM | 47 | 46 | 66 |
| Spunbond Basis wgt, GSM | 36 | 34 | 42 |
| Water Capacity, % | 179 | 500 | 263 |
| Water Rate, seconds | 60+ | 24.5 | 17.7 |
| Dynamic Coefficient of Friction | 0.37 | 0.44 | 0.55 |

As shown by the above data, the SMS (Comparison 2) is a hydrophobic laminate, having a water rate value of greater than 60 seconds (the test was terminated after this time). Further, the water capacity value for the SMS resulted, not from absorption of water, but from water droplets adhering to the surfaces of the exterior plies. Virtually no water absorption takes place.

The difference in the water capacity values between the absorbent thermal laminates of Example 1C and Example 2 is primarily due to the degree of contact between the spunbonded ply and the film. The Example 2 laminate has the polypropylene spunbonded ply in closer contact with the film ply, while the Example 1C laminate has a defined space bounded by the film and the polypropylene spunbonded ply. The space creates a reservoir for fluid, which contributes to greater fluid capacity.

Another difference between Example 1C and Example 2 above is in the coefficient of friction values. The greater value for Example 2 is attributed to inherent differences in the polymer selection and to the rougher exterior surface of the film, which is caused by the calcium carbonate filler. The roughened surface creates greater surface area to interact with the exposed surface of the polypropylene spunbonded ply.

EXAMPLE 3

A laminate was prepared by bonding a top ply of hydrophobic polypropylene spunbonded fabric having a basis weight of about 0.6 osy and a fluid impervious film. The film was a polyethylene film (Dow's Engage® 8002, melt index of 5 and a density of 0.87 gm/cc) filled with 55 wt % calcium carbonate (to impart breathability after stretching). The spunbonded ply and film were joined together using a hot melt adhesive. The polypropylene spunbonded was thermally bonded first, in the same manner as described in Example 1. The polypropylene spunbonded was then sprayed on one side with a 3 gram per square meter (gsm) layer of Rexene 2330 hot melt adhesive in fibrous form. The film was stretched to a final basis weight of 0.6 osy immediately before lamination. Lamination was achieved by applying the adhesive onto the polypropylene spunbonded fabric, pressing the polypropylene spunbonded fabric with the adhesive layer against the film before the hot melt lost its tackiness, followed by an embossing step similar to the calendering step described in Example 1 but with the pattern and anvil rolls being unheated. The embossed laminate was allowed to retract at least 10%. The laminate was then topically treated with a Alchovel/Glucopon surfactant mixture as in Example 2 (3:1 surfactant component ratio) to obtain a 0.5 wt % solids add-on.

Comparative data is given below for Sample A of Example 1 (Ex.1A) and Example 3 (Ex.3).

| Sample | Ex. 1A | Ex. 3 |
| --- | --- | --- |
| Laminate Basis Wgt, GSM | 33 | 42 |
| Spunbond Basis wgt, GSM | 24 | 22 |
| Water Capacity, | 671 | 356 |
| Water Rate, seconds | 40.7 | 17.3 |
| Dynamic Coefficient of Friction | 0.49 | 1.68 |

As shown above, the laminate is similar in water absorption to the thermally bonded laminates of Examples 1. More importantly, the laminate shows the contribution of film selection on the coefficient of friction values when measured with respect to the top side of the absorbent fabric, and hence, the impact on drape slippage. By using the Engage® low density polyethylene in the film, the dynamic coefficient of friction value of the polypropylene spunbonded ply against the film is increased approximately three fold, hence the resistance to slipping is increased by the same amount.

EXAMPLE 4

In order to increase the coefficient of friction value of the laminate of Example 1A, about 1.0 gsm of pressure sensitive adhesive was added to the exterior film surface of this sample. The pressure sensitive adhesive was sprayed onto the film surface in the form of discrete 1.5 mm squares, spaced 0.25 mm apart, by placing an open mesh screen over the exterior film surface and spraying a uniform coating of pressure sensitive adhesive. Removal of the mesh screen resulted in the pattern of discrete squares. The impact on the coefficient of friction value (for polypropylene spunbonded fabric slipping against the film with the non-slip adhesive pattern) is shown below.

| Sample | Ex. 1A | Ex. 4 |
| --- | --- | --- |
| Laminate Basis Wgt, GSM | 33 | 34 |
| Spunbond Basis wgt, GSM | 24 | 22 |
| Water Capacity, % | 671 | 584 |
| Water Rate, seconds | 40.7 | 48 |
| Dynamic Coefficient of Friction | 0.49 | 2.80 |

EXAMPLE 5

A pressure sensitive adhesive was applied to the laminate of Example 2 in the same manner as described for Example 6 to make a hydrophilic polypropylene spunbonded and breathable film laminate with an anti-slip coating. For this sample the amount of pressure sensitive adhesive added to the total basis weight of the laminate was about 2 gsm. The result was an increase in the coefficient of friction value for the film, measured against the top side of the absorbent fabric, as shown below.

| Sample | Ex. 2 | Ex. 5 |
| --- | --- | --- |
| Laminate Basis Wgt, GSM | 66 | 68 |
| Spunbond Basis wgt, GSM | 42 | 42 |
| Water Capacity, % | 263 | 240 |
| Water Rate, seconds | 17.7 | 14.2 |
| Dynamic Coefficient | 0.55 | 2.1 |

What is claimed is:

1. An absorbent surgical drape comprising:
   an outer layer of a hydrophilic meltspun fabric; and
   an inner layer, adapted to contact a patient, of a liquid impervious film;
   wherein the film is bonded to the meltspun fabric and a test of dynamic coefficient of friction, as measured by test method ASTM D1894-95, between the outer layer and the inner layer yields a value of greater than 0.4.

2. The surgical drape of claim 1, wherein the meltspun fabric comprises a spunbonded fabric.

3. The surgical drape of claim 2, wherein the spunbonded fabric includes a hydrophilic chemical additive.

4. The surgical drape of claim 3, wherein the hydrophilic spunbonded fabric contains filaments having a hydrophilic chemical additive therein.

5. The surgical drape of claim 3, further comprising a meltblown layer.

6. The surgical drape of claim 1, wherein the film has a basis weight of less than about 25 gsm.

7. The surgical drape of claim 1, wherein the hydrophilic meltspun fabric comprises a meltblown fabric which includes a hydrophilic chemical additive.

8. The surgical drape of claim 7, wherein the chemical additive phase separates and migrates toward the surface of the polymer fiber.

9. The surgical drape of claim 7, wherein the chemical additive is selected from the following group: polyoxyalkylene modified fluorinated alkyls, polyoxyalkylene fatty acid esters, polyoxyalkylene modified polydimethyl siloxanes, polyethylene glycol modified terephthalate, or ethoxylated alkyl phenols.

10. The surgical drape of claim 1, wherein the film has a dynamic coefficient of friction, as measured by test method ASTM D1894-95 between the outer layer and the inner layer of greater than 0.7.

11. The surgical drape of claim 1, wherein the film has an exposed surface which is at least partially coated with an anti-slip coating to increase the dynamic coefficent of friction, as measured by test method ASTM D1894-95, between the outer layer and the inner layer.

12. The surgical drape of claim 11, wherein the film has a dynamic coefficient of friction, as measured by test method ASTM D1894-95, between the outer layer and the inner layer of greater than 0.70.

13. The surgical drape of claim 12 wherein the film has a dynamic coefficient of friction, as measured by test method ASTM D1894-95, between the outer layer and the inner layer of greater than 1.0.

14. The surgical drape of claim 1, wherein the film is a breathable film.

15. The surgical drape of claim 1, wherein the film is attached to the meltspun fabric in a stretched condition and subsequently released to form a void space between the film and fabric.

16. The surgical drape of claim 1, wherein the drape, tested per NFPA 702-1980, meets the 20 second or greater flame propagation criteria for a Class 1 material.

17. The surgical drape of claim 1, wherein the anti-slip coating is applied to the exposed surface of the film by a method selected from the following group: solution coating, gravure coating or printing coating.

18. A method of making an absorbent surgical drape comprising the steps of:

forming an outer layer of a hydrophilic meltspun fabric; and attaching an inner layer of a liquid impervious film to one surface of the hydrophilic meltspun fabric;

wherein the film is bonded to the meltspun fabric and a test of dynamic coefficient of friction, as measured by test method ASTM D1894-95, between the outer layer and the inner layer yields a value of greater than 0.4.

19. The method of claim 18, further comprising:

coating a portion of an exposed surface of the film with a material to increase the coefficient of friction of the film surface.

20. The method of claim 19 wherein the material applied to the exposed surface of the film is an adhesive.

21. The method of claim 18, wherein forming the hydrophilic meltspun fabric comprises:

adding one or more hydrophilic chemical additives to a polymer melt; and forming a spunbonded fabric of continuous filaments from the polymer melt.

22. The method of claim 18, wherein the drape, tested per NFPA 702-1980, meets the 20 second or greater flame propagation criteria for a Class 1 material.

23. An absorbent surgical drape comprising:

an outer layer of a hydrophilic meltspun fabric; and an inner layer, adapted to contact a patient, of a liquid impervious film, the film having an exposed surface which is at least partially coated with an anti-slip coating;

wherein the film is bonded to the meltspun fabric and a test of dynamic coefficient of friction, as measured by test method ASTM D1894-95, between the outer layer and the exposed surface of the inner layer yields a value of greater than 1.0.

24. The surgical drape of claim 17 wherein the anti-slip coating is applied to the exposed surface of the film in a pattern.

* * * * *